(12) United States Patent
St-Amour et al.

(10) Patent No.: US 7,304,311 B2
(45) Date of Patent: Dec. 4, 2007

(54) WHOLE PRINTING MEDIUM EVALUATION METHOD AND DEVICE

(75) Inventors: Robert St-Amour, Montreal (CA); Christine Canet, Saint-Adolphe d'Howard (CA); Karine Lapointe, Laval (CA)

(73) Assignee: Institut des Communications Graphiques du Quebec, Montreal, Quebec (CA)

( * ) Notice: Subject to any disclaimer, the term of this patent is extended or adjusted under 35 U.S.C. 154(b) by 41 days.

(21) Appl. No.: 10/656,309

(22) Filed: Sep. 5, 2003

(65) Prior Publication Data

US 2005/0030546 A1    Feb. 10, 2005

(30) Foreign Application Priority Data

Sep. 6, 2002    (CA)    .................................... 2399472

(51) Int. Cl.
*G01T 3/00*    (2006.01)

(52) U.S. Cl. ............................ 250/390.07; 250/339.07; 250/339.08; 250/339.09; 702/30; 702/27; 422/62; 436/171

(58) Field of Classification Search ........... 250/390.07, 250/339.07, 339.08, 339.09; 702/30, 27; 436/171; 422/62
See application file for complete search history.

(56) References Cited

U.S. PATENT DOCUMENTS

| | | | |
|---|---|---|---|
| 4,935,628 A | | 6/1990 | Martin et al. |
| 5,060,572 A | | 10/1991 | Waizmann |
| 5,373,366 A | | 12/1994 | Bowers |
| 5,446,681 A | | 8/1995 | Brown et al. |
| 5,578,824 A | * | 11/1996 | Koguchi et al. ............ 250/318 |
| 5,967,033 A | | 10/1999 | Pfeiffer et al. |
| 6,070,128 A | * | 5/2000 | Descales et al. ............... 702/30 |
| 6,275,285 B1 | | 8/2001 | Nottke et al. |
| 6,287,374 B1 | | 9/2001 | Yanagida et al. |
| 6,784,428 B2 | * | 8/2004 | Rabolt et al. .......... 250/339.02 |
| 6,849,460 B2 | * | 2/2005 | McFarland et al. ......... 436/171 |
| 2001/0043329 A1 | * | 11/2001 | Hustert ....................... 356/402 |
| 2001/0055052 A1 | * | 12/2001 | Mueller et al. ............... 347/88 |
| 2002/0048654 A1 | * | 4/2002 | Yoshino et al. ............. 428/195 |
| 2005/0031910 A1 | * | 2/2005 | Schwartz et al. ........... 428/702 |

FOREIGN PATENT DOCUMENTS

| | | |
|---|---|---|
| JP | 60 202172 | 10/1985 |
| JP | 60202172 | 10/1985 |
| JP | 03 238 345 | 10/1991 |
| JP | 3238345 | 10/1991 |
| WO | 97 05 483 | 2/1997 |

OTHER PUBLICATIONS

R. Merrill et al.; Analysis of Ballpoint Pen Inks by Diffuse Reflectance Infrared Spectrometry, Journal of Forensic Sciences, JFSCA, vol. 37, No. 2, Mar. 1992, pp. 528-541.

* cited by examiner

Primary Examiner—David Porta
Assistant Examiner—Christine Sung
(74) Attorney, Agent, or Firm—Fay Kaplun & Marcin, LLP

(57) ABSTRACT

A method and device for evaluating a printing medium for use in a printing process, in which a set of spectral data is generated from a sample of the printing medium, and the set of spectral data is analysed. The analysis of the set of spectral data comprises detecting spectral data of the set indicative of features of the printing medium related to performance of that printing medium in the printing process. The performance of the printing medium in the printing process is predicted in response to the detected spectral data of the set indicative of performance-related printing medium features, and the printing medium is accepted or refused for use in the printing process in response to this printing medium performance prediction.

48 Claims, 10 Drawing Sheets

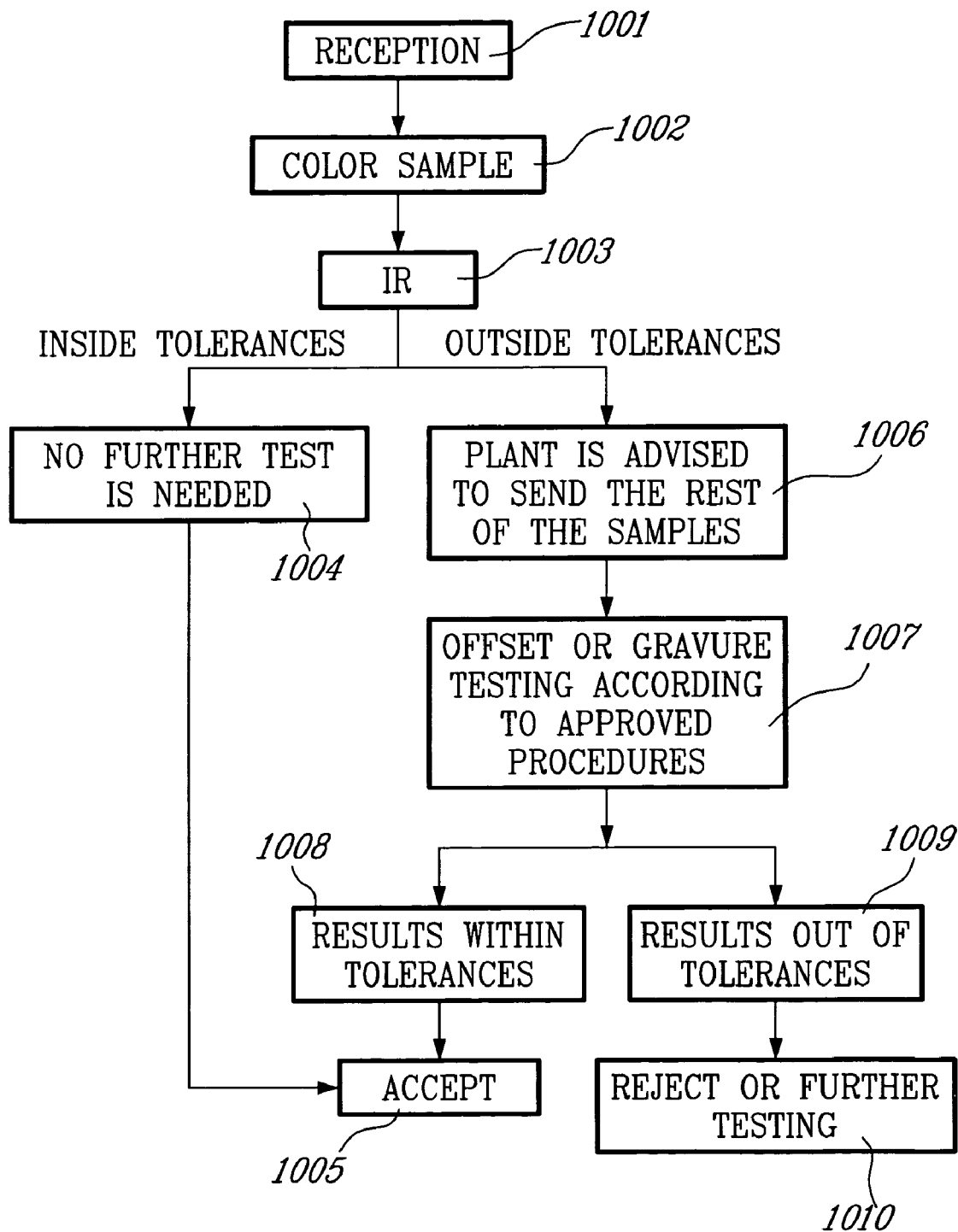

WHOLE PRINTING MEDIUM EVALUATION METHOD AND DEVICE

FIELD OF THE INVENTION

The present invention relates to a method and device for evaluating a printing medium for use in a printing process. More specifically but not exclusively, the present invention contemplates a method and device for predicting the quality, features and/or performance of a printing medium, such as an ink or dye, in a printing process, in order to accept or reject the printing medium for use in a printing process.

BACKGROUND OF THE INVENTION

Although ink supplies represent the second highest expense, after substrates (such as paper, cardboard, etc.), for the production of printed products, little care and efforts have been devoted so far to control the features of these ink supplies and their impact on production costs and quality. For instance, slight changes in ink formula can result in an important reduction of performance and/or efficiency, leading to substantial but hardly identifiable ink consumption and cost increases. For a large printing plant, such variations in ink quality may result in millions of dollars of extra costs annually. Furthermore, introduction of improper ink in a printing process may require stopping and cleaning of a press, which is highly troublesome and costly.

In an attempt to obviate the aforementioned drawbacks, some quality control is carried out on printed samples or on whole (unprinted wet state as supplied by manufacturers, or diluted, or bleached) ink samples. However, while evaluation of printed samples (generally by simple photometric measurements) produces a late indication of a problem and mainly addresses visual quality problems, testing whole ink samples prior to printing is typically carried out in laboratory through an extensive series of physical and mechanical tests, such as strength of ink, opacity, viscosity, etc., requiring fair amounts of ink and time. Furthermore, differences between the physical or mechanical properties of a sample with respect to reference values do not provide clear indication of the resulting impact on in-process performance of the tested ink.

For instance, U.S. Pat. No. 5,967,033, issued to Pfeiffer et al., on Oct. 19, 1999 discloses a method for determining ink coverage in a print image by analysis of an optical signal in the visible and near-infrared domain, reflected from a printed substrate. Similarly, in U.S. Pat. No. 4,935,628 (Martin et al.) issued on Jun. 19, 1990, ink from a writing instrument dried on a substrate is irradiated at multiple frequencies in the visible and infrared spectra, and the reflected signal is analysed for differentiation and authentication purposes by comparison with reference signals from a database. U.S. Pat. No. 6,275,285 granted to Nottke et al. on Aug. 14, 2001, also teaches a method for authentication of an ink sample dried on a substrate, but uses RAMAN spectrometry to obtain a higher level of resolution and discrimination of ink spectral signatures.

In U.S. Pat. No. 5,373,366 granted to Bowers on Dec. 13, 1994, concentration of a liquid ink sample is measured through illumination of the sample with a LED (Light Emitting Diode) and analysis of the direct and reflected optical signal using photodiodes. In a similar manner, Japanese Publication No. 60-202172A (Sato et al.) dated Dec. 10, 1985, discloses an ink production unit wherein liquid ink samples are analysed by UV/Visible spectrophotometry to provide indication of the density and appropriate feedback is supplied to the production unit for adjustment of the dilution rate. In U.S. Pat. No. 6,287,374 granted to Yanagida et al. on Sep. 11, 2001, wetting properties of a pigment in a water base liquid ink are measured by infrared spectrometry. In Japanese Publication No. 03-238345A, concentration of residual ink in paper pulp is measured by analysis of the signature of ink absorption in the near-infrared spectrum.

It should be mentioned that most of the above discussed prior technologies are concerned with jet-printing inks and writing instrument inks and that technologies used in connection with offset printing inks or the like are generally of the spectrophotometric type. Therefore, none of the above-discussed existing techniques provide an appropriate means for evaluating features and quality of a whole printing ink, and especially with regard to in-process performance. However, the above-mentioned references teach that infrared (IR) and near-infrared (NIR) spectrometry enable extended characterization of ink, providing sort of distinctive signature (also referred to as fingerprint). Such techniques also proved to be very effective for chemometric analysis of organic components such as resins, pigments or solvents found in media such as paints, dyes and inks, as well as for quality control in the pharmaceutical industry.

A few scientific publications confirm that Fourier Transform InfraRed (FT-IR) and Fourier Transform Near-Infra-Red (FT-NIR) spectra of a liquid ink solution provide a unique signature, usable for authentication purposes. For instance, Rena A. Merrill and Edward G. Bartick stated in an article entitled "Analysis of Ballpoint Pen inks by Diffuse Reflectance Infrared Spectrometry" (Journal of Forensic Sciences, JFSCA, Vol. 37, No 2, March 1992, pp 528-541), that Diffuse Reflectance (DR) Fourier Transform Infrared Spectrometry (FT-IR) provides good results in matching spectra from ink solutions extracted from a questioned document with spectra from pure whole writing ink samples from a data base for identification purposes. The major cause of errors upon using this technique is related to the presence of substrate traces in the extracted ink solution.

Although the above examples show that methods exist to detect or evaluate ink properties, none of these methods is readily applicable to evaluation of a whole printing ink to reliably predict the in-process functional characteristics thereof and identify any features susceptible to negatively affect the performance of the ink(s) in a printing process such as offset, gravure, flexography, etc.

Thus a need exists for a technique that not only overcomes the limitations and drawbacks of the above-described methods, but that can be carried out using a very small sample from a whole printing ink supply, to provide indication of the degree of compliance with reference ink data and predict in-process performance characteristics prior to introduction of the ink into the actual process.

SUMMARY OF THE INVENTION

In accordance with the present invention, there is provided a method of evaluating a printing medium for use in a printing process, comprising:

generating a set of spectral data from a sample of the printing medium; and analysing the set of spectral data, wherein analysis of the set of spectral data comprises:

detecting spectral data of the set indicative of features of the printing medium related to performance of the printing medium in the printing process; and predicting the performance of the printing medium in the printing process in response to the detected spectral data of the set indicative of performance-related printing medium features.

The present invention relates to a device for evaluating a printing medium for use in a printing process, comprising:

means for generating a set of spectral data from a sample of the printing medium; and means for analysing the set of spectral data, wherein the analysing means comprises:
  means for detecting spectral data of the set indicative of features of the printing medium related to performance of that printing medium in the printing process; and
  means for predicting the performance of the printing medium in the printing process in response to the detected spectral data of the set indicative of performance-related printing medium features.

The present invention is further concerned with a device for evaluating a printing medium for use in a printing process, comprising:
a generator of a set of spectral data from a sample of the printing medium; and
an analyser of the set of spectral data, wherein the analyser comprises:
  a detector of the spectral data of the set indicative of features of the printing medium related to performance of the printing medium in the printing process; and
  a predictor of the performance of the printing medium in the printing process in response to the detected spectral data of the set indicative of performance-related printing medium features.

The foregoing and other objects, advantages and features of the present invention will become more apparent upon reading of the following non restrictive description of an illustrative embodiment thereof, given by way of example only with reference to the accompanying drawings.

BRIEF DESCRIPTION OF THE DRAWINGS

In the appended drawings:

FIG. 10 is a flow chart of an extensive printing medium evaluation method, according to the illustrative embodiment of the present invention.

DETAILED DESCRIPTION OF THE ILLUSTRATIVE EMBODIMENT

The illustrative embodiment of the printing medium evaluation method and device according to the present invention will now be described with reference to the appended drawings. Although the illustrative embodiment of the present invention will be described in relation to a non-restrictive application of the evaluation method and device to whole printing ink, it should be kept in mind that the present invention may also be applied to other types of printing medium, for example dyes and jet-printing ink.

Whole printing ink evaluation according to the illustrative embodiment of the present invention basically consists of obtaining a set of spectral data from a sample of whole printing ink and analyzing this set of spectral data to predict the performance of the ink in a printing process. The whole printing ink will then be accepted or rejected depending on this prediction.

Figure 1:
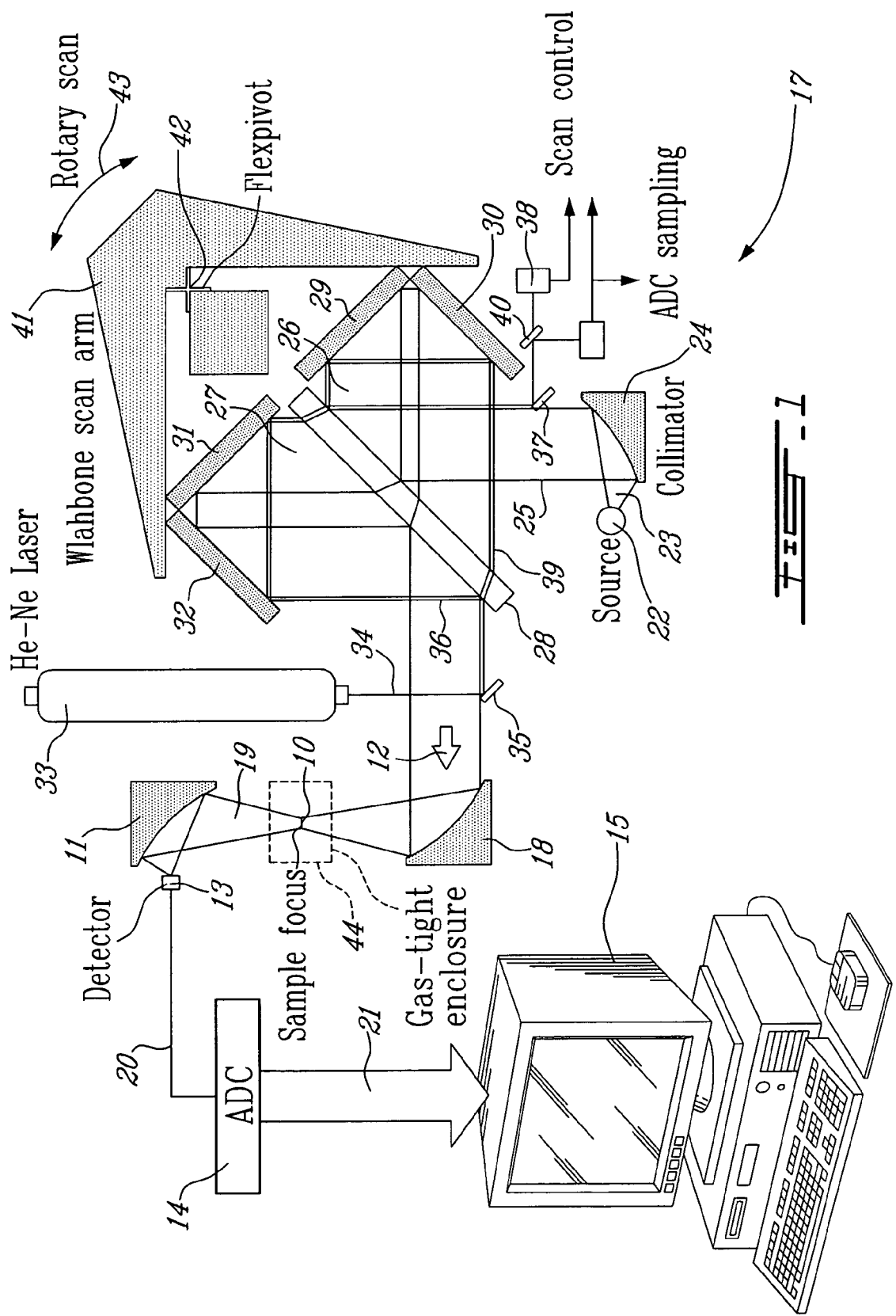
FIG. 1 is a schematic diagram of a typical set-up for obtaining FT-IR spectral data from a whole printing medium sample, according to the non-restrictive illustrative embodiment of the method and device according to the present invention.

Complete, accurate, repeatable and distinctive signatures can be obtained by submitting whole printing ink samples to Fourier Transform-InfraRed (FT-IR) interferometric analysis according to a test set-up of the type as illustrated in FIG. 1, representing a typical interferometer system 17. In the same manner, complete, accurate, repeatable and distinctive signatures could be obtained by submitting whole printing ink samples to Fourier Transfor-Near-Infrared (FT-NIR) interferometric analysis according to the test set-up of FIG. 1.

Figure 6:
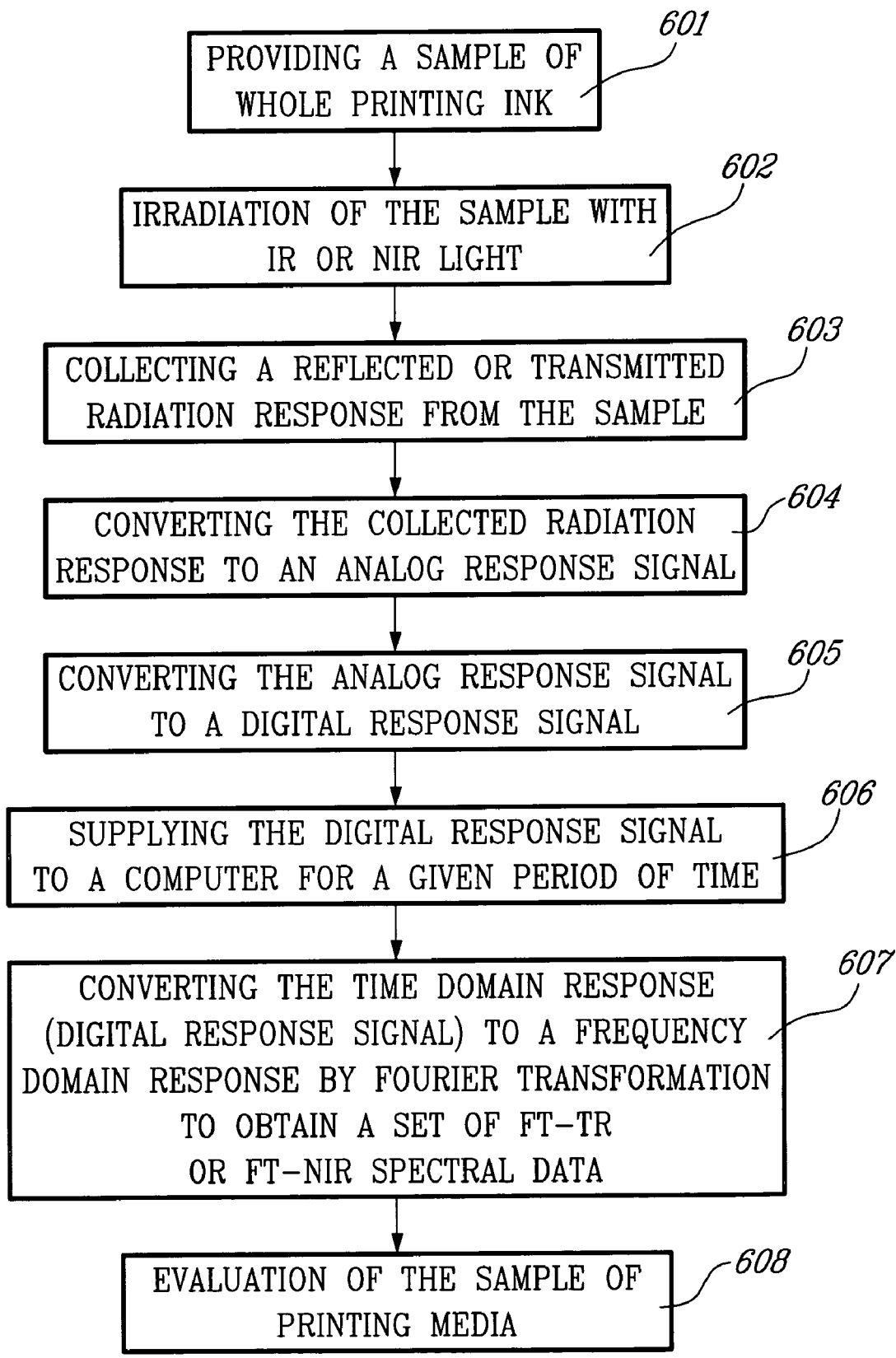
FIG. 6 is a flow chart of the non-restrictive illustrative embodiment of the printing medium evaluation method according to the present invention.

Referring to FIG. 1, a sample 10 consisting of a drop or small quantity of whole printing ink is drawn from a supply of whole printing ink (step 601 of FIG. 6). The sample 10 is irradiated with light (step 602) in a specific spectral range of the infrared (IR) frequency spectrum. Analysis could also be conducted in the near-infrared (NIR) spectrum, providing different and complementary sets of spectral data.

Referring back to FIG. 1, collimated light 12 is generated. To generate collimated light 12 in a specific spectral range of the infrared (IR) frequency spectrum, the interferometer system 17 comprises an infrared light source 22. Diverging infrared light 23 from the source 22 is collimated by reflection onto a collimator 24 to produce a collimated light beam 25.

The collimated light beam 25 is divided into two collimated light beam portions 26 and 27 that interfere with each other to generate collimated light 12 within a specific spectral range of the IR frequency spectrum. For that purpose, beam splitter 28 reflects a portion of the light beam 25 to form light beam portion 26 but propagates the other portion of the light beam 25 to produce light beam portion 27. Light beam portion 26 successively reflects on mirrors 29 and 30 and propagates through beam splitter 28 and, then toward concave mirror 18. Regarding light beam portion 27, it successively reflects on mirror 31, mirror 32 and beam splitter 28 to propagate toward the concave mirror 18.

Before reaching the concave mirror 18, the light beam portions 26 and 27 interfere with each other to produce collimated light 12 in a specific spectral range of the IR frequency spectrum. Interference between the light beam portions 26 and 27 is caused by a difference of the distance of propagation from the source 22 of the two light beam portions 26 and 27. This difference of distance of propagation is accurately controlled to obtain, by interference between the two light beam portions 26 and 27, collimated light 19 within the desired specific spectral range of the IR spectrum.

As illustrated in FIG. 1, the beam splitter 28 and the mirrors 29-32 are mounted on a wishbone scan arm 41 itself mounted on a flexpivot 42.

To accurately control the difference of distance of propagation, a laser 33, for example a He—Ne laser, is used to generate a laser beam 34 reflected on a mirror 35. Then, a portion 36 of the laser beam 34 from the mirror 35 is reflected on the beam splitter 28, successively reflects on the mirrors 32 and 31 and propagated through the beam splitter 28 toward a mirror 37. The laser beam portion 36 is then reflected by mirror 37 and propagates through a beam splitter 40 toward a scan control 38. Another portion 39 of the laser beam 34 from the mirror 35 propagates through the beam splitter 28, successively reflects on mirror 30, mirror 29, beam splitter 28, and mirror 37 to propagate through the beam splitter 40 toward the scan control 38.

The difference of distance of propagation between the laser beam portions 36 and 39 is representative of the difference of distance of propagation between the light beam portions 26 and 27 to thereby allow the scan control 38 to control rotary scan movement (see arrow 43) of the wishbone scan arm 41 about the flexpivot 42 in view of accurately controlling the difference of distance of propagation between the light beam portions 26 and 27 and thereby obtaining, by interference between the two light beam portions 26 and 27, collimated light 18 in the specific spectral range of the IR frequency spectrum.

The collimated light 12 is then focused toward the whole printing ink sample 10 by reflection on the concave mirror 18. Energy from the light 12 is selectively absorbed by chemical elements of the whole printing ink sample 10 and a unique time distributed scattered radiation response 19 for a given ink formula is produced by propagation of the focused light 12 through the sample 10 and is collected by a concave mirror 11 (step 603). The concave mirror 11 reflects and focuses the collected, time distributed scattered radiation response 19 toward an infrared detector 13. This infrared detector 13 converts the collected, time distributed scattered radiation response 19 to an analog response signal 20 (step 604). This analog response signal 20 is finally converted to a digital response signal 21 through an analog-to-digital (A/D) converter 14 before being supplied to a computer 15 for a given period of time (step 606).

The time domain response (digital response signal) as supplied to the computer 15 from the A/D converter 14 is mathematically converted to a frequency domain response by Fourier transformation (Step 607). This provides a set of FT-IR spectral data that can be represented under an energy/frequency pattern, for example a graph of the absorbance "versus" wave number ($cm^{-1}$) as shown in FIGS. 2-5. Sets of spectral data representative of a plurality of different whole ink samples can be stored in a database (library) of the computer 15 and can be transferred to another computer (not shown) for comparison, analysis or other purpose.

Different ways of mounting the sample 10 of whole printing ink into the interferometer 17 can be contemplated. As a first example, directing light radiation toward the sample at an angle and collecting the reflected scattered light radiation response (diffuse reflectance) provides a spectrum that is rather representative of the chemical elements at the surface of the sample. Alternatively, as a second example as illustrated in FIG. 1, the scattered radiation response resulting from light propagated through the whole printing ink sample 10 can be collected, providing a spectrum better representative of the whole printing ink formula. Transmission measurements can be advantageously carried out with the sample 10 of whole printing ink enclosed in a gas-tight enclosure 44 (FIG. 1), to thereby prevent evaporation of volatile ink components; in this manner maximal information and, in turn, optimal discrimination between two closely similar samples can be obtained.

Figure 2:
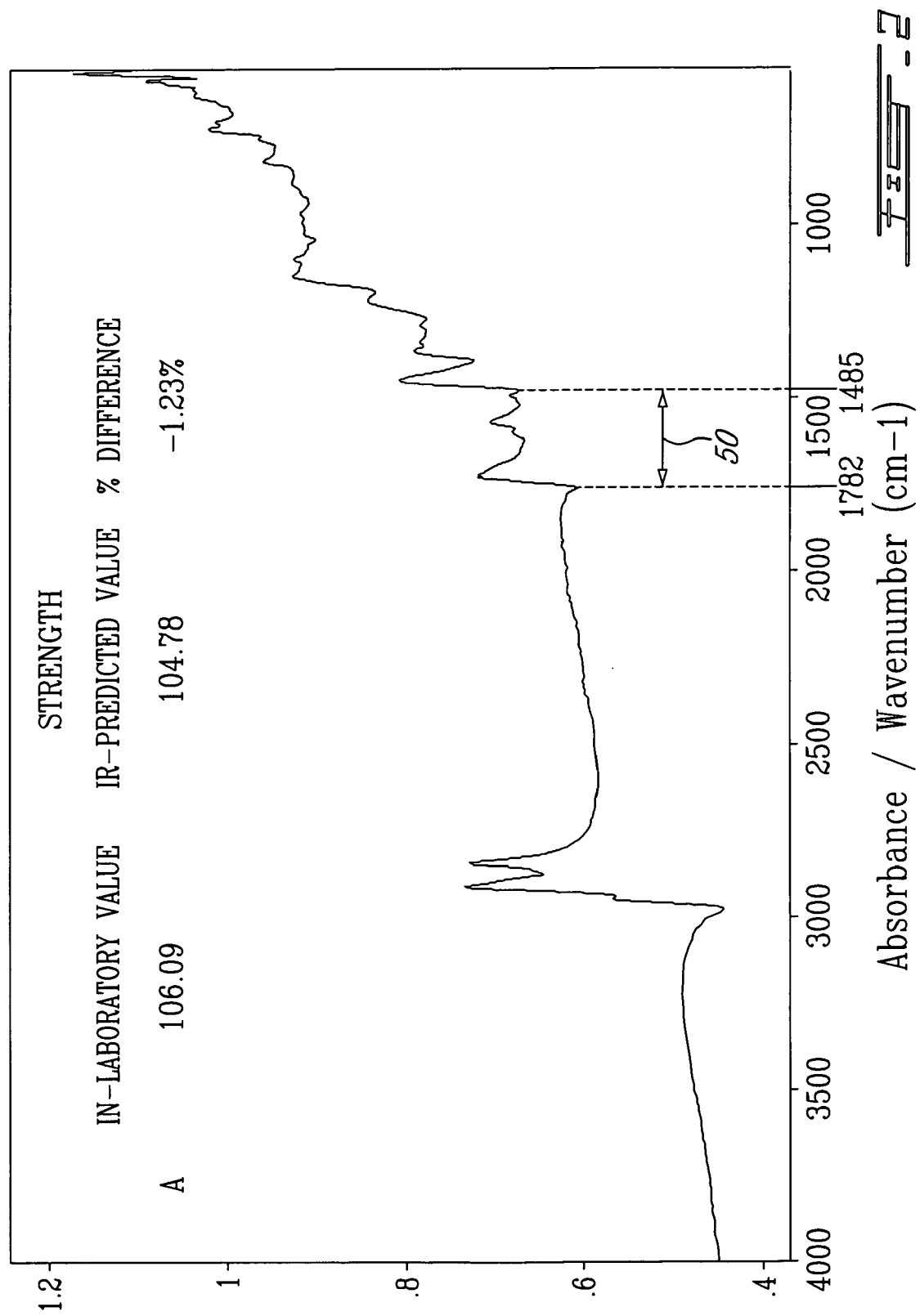
FIG. 2 is a FT-MIR (Fourier Transform-Mid-InfraRed) graph of the absorbance "versus" wave number ($cm^{-1}$) obtained from and representative of a sample of a first supply of whole printing ink (black)
Figure 3:
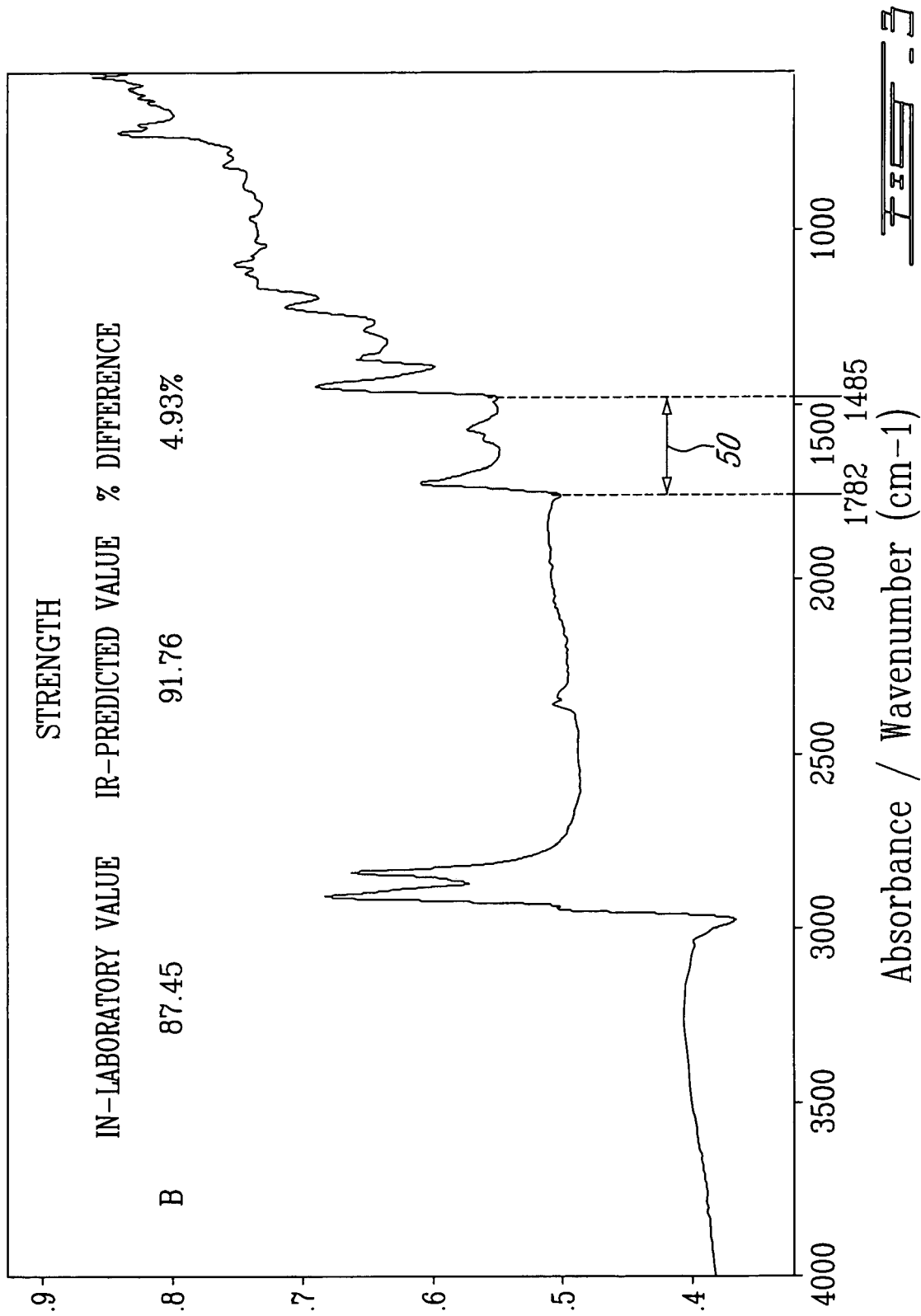
FIG. 3 is a FT-MIR (Fourier Transform-Mid-InfraRed) graph of the absorbance "versus" wave number ($cm^{-1}$) obtained from and representative of a sample of a second supply of whole printing ink (black)
Figure 4:
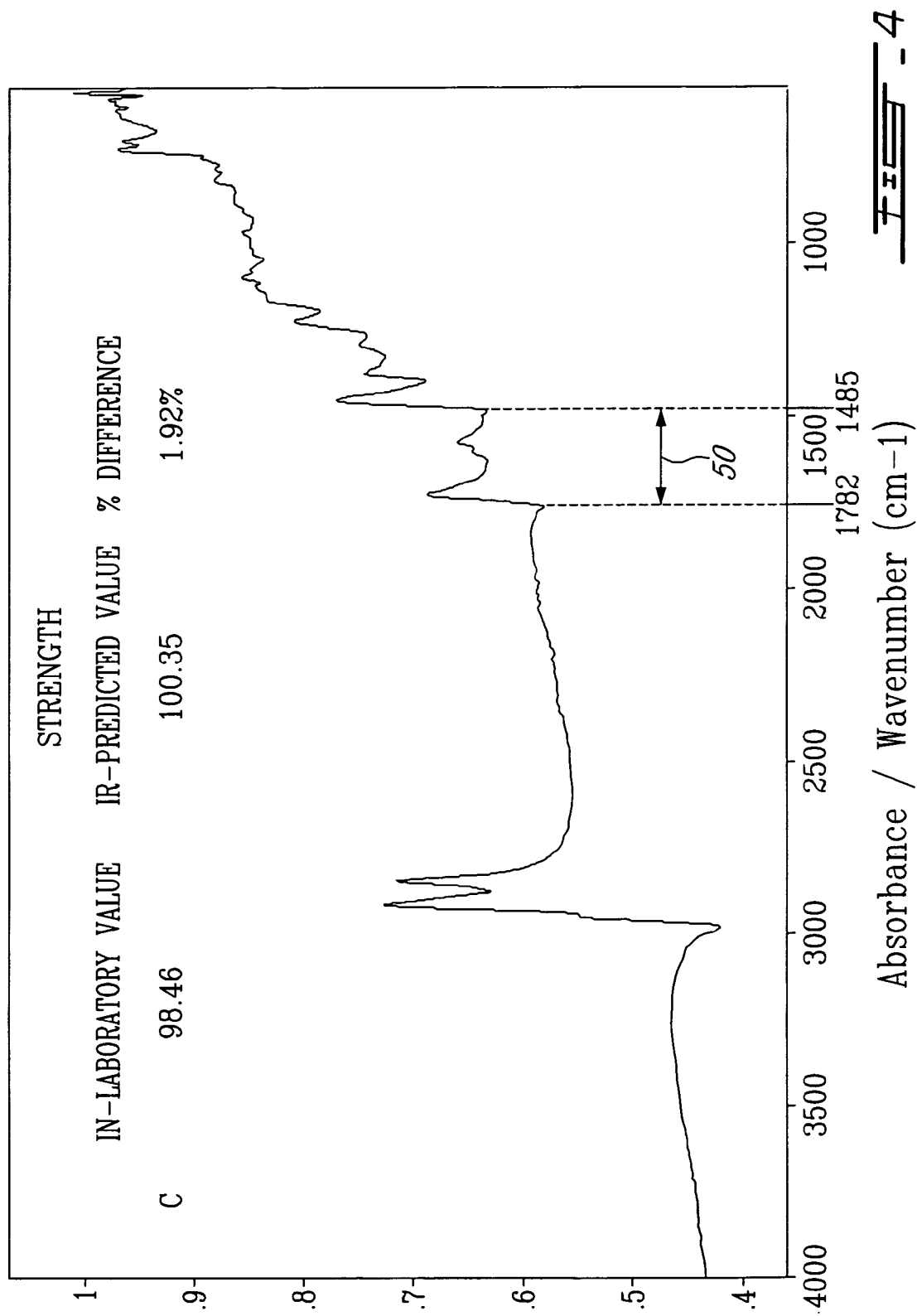
FIG. 4 is a FT-MIR (Fourier Transform-Mid-InfraRed) graph of the absorbance "versus" wave number ($cm^{-1}$) obtained from and representative of a sample of a third supply of whole printing ink (black)
Figure 7:
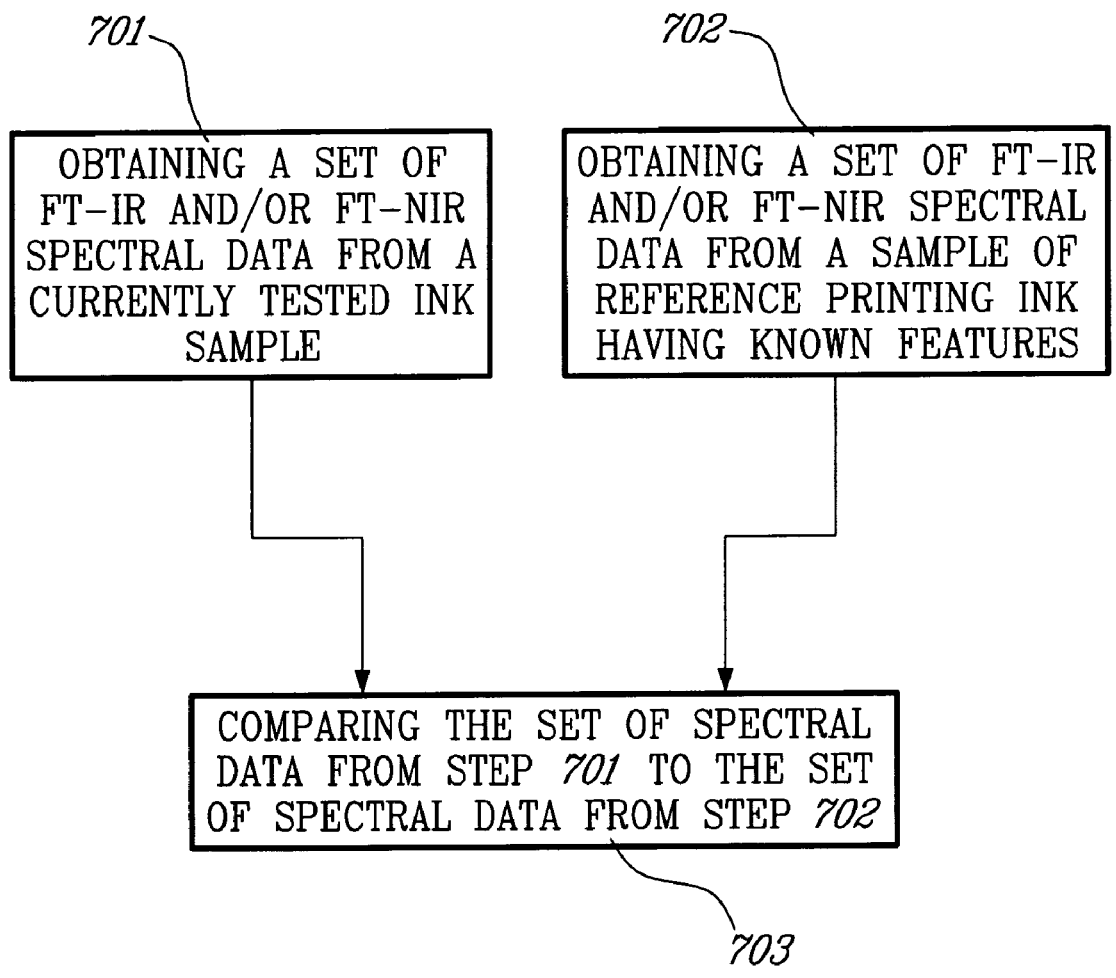
FIG. 7 is a flow chart illustrating evaluation of a sample of whole printing medium in accordance with the illustrative embodiment of the present invention.

The illustrative embodiment of the printing ink evaluation method and device contemplates a first technique for providing an evaluation (step 608) of a sample of whole printing ink from a given ink supply, for example a given production batch. In accordance with this first technique as illustrated in FIG. 7, a set of FT-IR and/or FT-NIR spectral data as represented in FIG. 2-4 is first obtained from a currently tested whole printing ink sample (step 701 of FIG. 7). This set of FT-IR and/or FT-NIR spectral data is then compared (step 703) with a set of FT-IR and/or FT-NIR data as represented in FIGS. 2-4 and obtained from a sample of whole printing ink from a reference (master) supply having known features (step 702).

The illustrative embodiment of the printing ink evaluation method and device contemplates a second technique for providing an evaluation (step 608 of FIG. 6) of a sample of whole printing ink from a given ink supply. In accordance with this second technique, a difference between a set of spectral data from a currently tested sample of whole printing ink and a set of spectral data from a sample of a reference whole printing ink is detected for example by arithmetic difference to emphasize deviations between respective intensities of both sets of spectral data (step 806). Accordingly, depending on whether the deviations are located within previously defined tolerance criteria, matching of the reference features by the evaluated ink supply can be determined to accept or reject the currently evaluated ink supply for use in a printing process (step 807).

Figure 8:
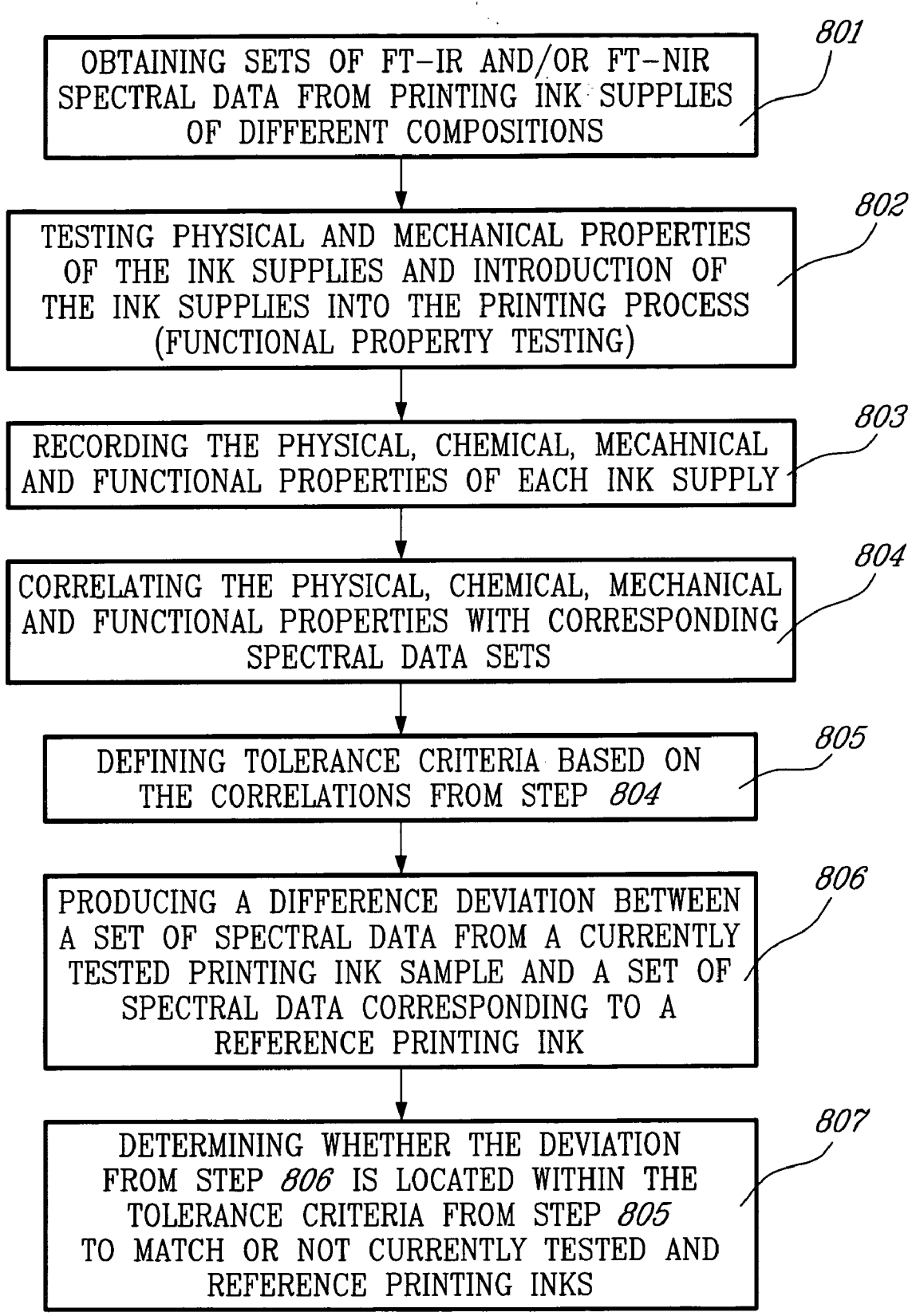
FIG. 8 is a flow chart illustrating evaluation of a sample of whole printing medium in accordance with the illustrative embodiment of the present invention.

Definition of the tolerance criteria is the result of extensive experimentation. Sets of FT-IR (and eventually FT-NIR) spectral data from numerous whole printing ink supplies of slightly different chemical compositions were obtained (step 801), followed by testing physical and mechanical properties of these ink supplies and introduction of the ink supplies into a printing process to test their functional properties (step 802). Physical (for example tack, density, strength, viscosity, etc.), chemical (for example, resin, solvent, pigment, etc.), mechanical and functional (for example coverage, mileage, etc.) properties (features) of each ink supply were recorded (step 803) and correlated with the corresponding sets of spectral data. The latter correlations enabled prediction of the impact on ink features of deviations with respect to a reference accepted (master) batch with a sufficient level of confidence to accept or reject the whole printing ink supply. Tolerance criteria can therefore be defined from these correlations (step 805 of FIG. 8) to accept only whole printing ink supplies of adequate quality and performance.

Figure 9:
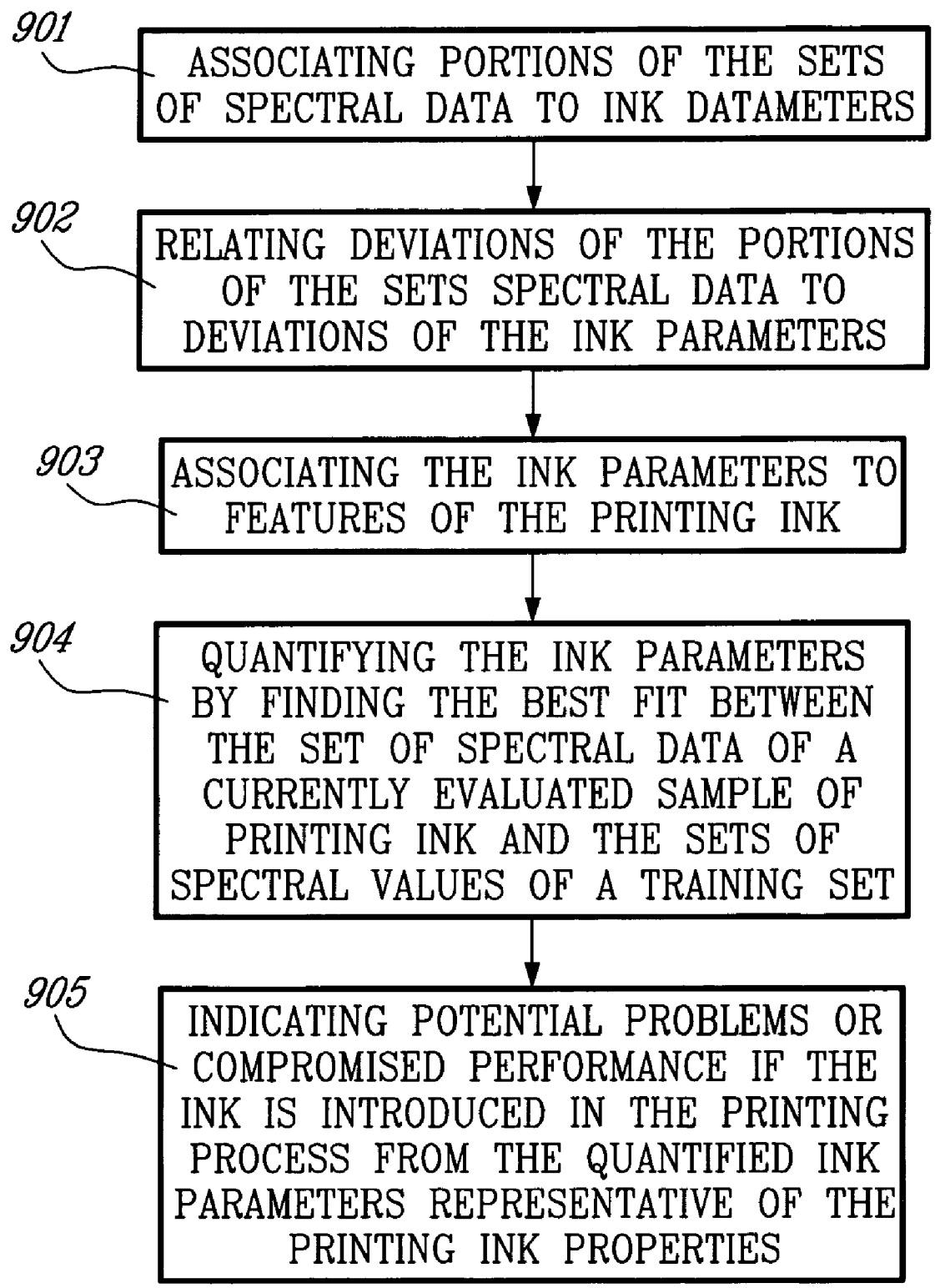
FIG. 9 is a flow chart of a method of detecting potential problems or compromise performance if the printing medium is introduced in a printing process, according to the illustrative embodiment of the present invention.

Moreover, training sets can be constructed for each of a plurality of ink parameters, to indicate variations of the value of these parameters through detection of variations (such as variations of peak amplitude, shape, position, etc.) in the spectrums (sets of spectral data). More specifically, the know how developed through experimentation enables some parametric analysis of a superposition of spectra (for example FIG. 5) or direct parametric analysis of a spectrum as represented for example in FIGS. 2-4. For that purpose, portions (for example frequency bandwidth) of the differential or original sets of spectral data are associated to ink parameters (step 901 of FIG. 9). Deviations of these portions of the sets of spectral data in amplitude, shape, shifting, etc. are related to deviations of the ink parameters (step 902). These ink parameters are associated with features of the whole printing ink supply (step 903) and are indicative of potential problems or compromised performance if introduced into the printing process (Step 905). A training set can be used to quantify an ink parameter by finding the best fit between a set of spectral data corresponding to a currently evaluated sample of whole printing ink and the sets of spectral data of a corresponding training set (step 904), or by an algorithm elaborated to directly predict the value (quantify) of a feature of an ink sample by multivariable parametric analysis of its spectrum, based on the knowledge provided by a given training set.

Figure 5:
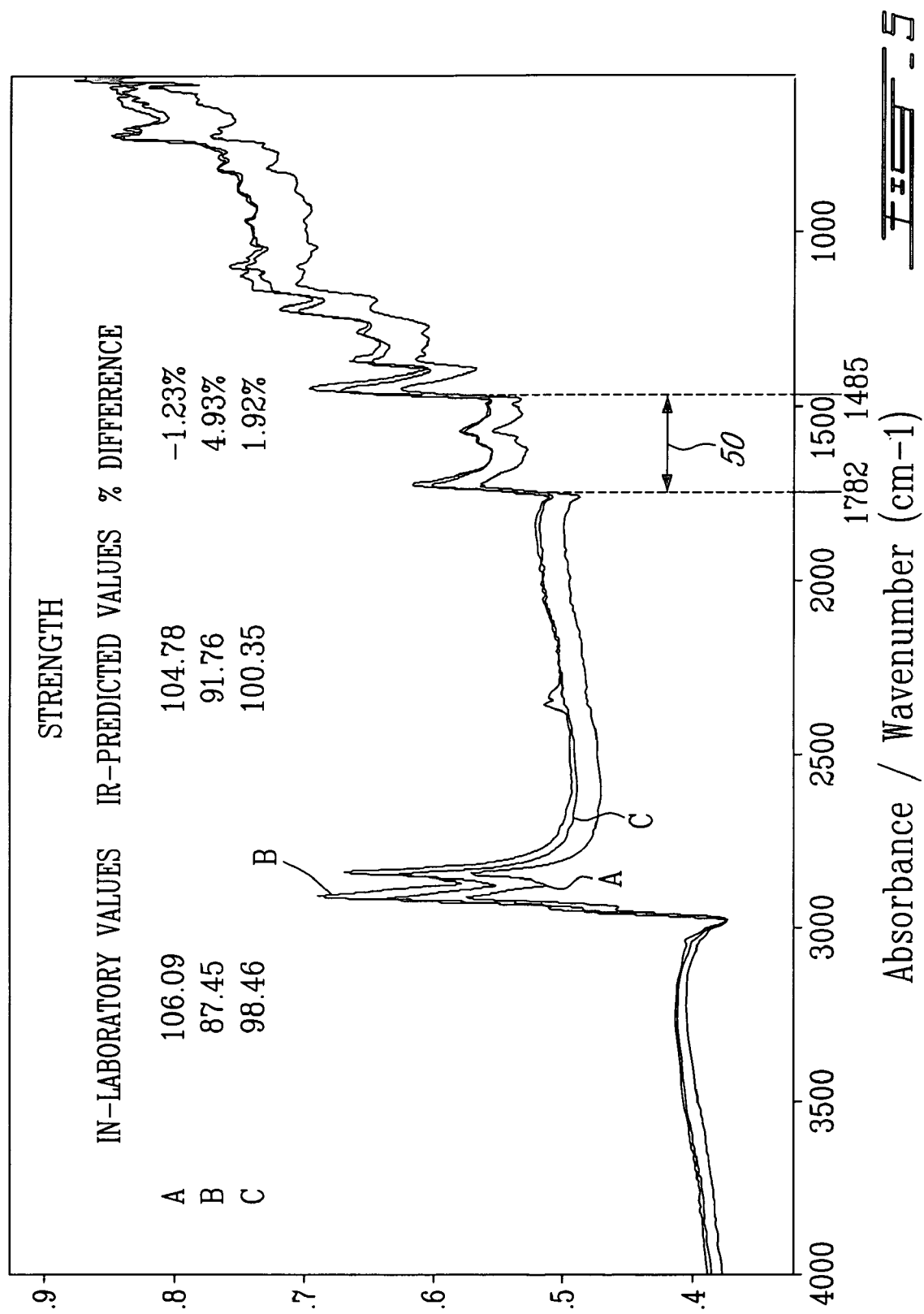
FIG. 5 is a graph resulting from a superposition of the three (3) FT-MIR (Fourier Transform-Mid-InfraRed) curves of FIGS. 2-4 (absorbance "versus" wave number ($cm^{-1}$))

For example, FIG. 5 shows that, in the region 50 of the spectrum, the lower the absorbance, the higher the strength.

Indeed, the curve A of FIG. 2 of lower absorbance in the region 50 of the spectrum corresponds to a higher strength (in-laboratory value of 106.09 and IR-predicted value of 104.78 for a difference of −1.23%) whole printing ink. The curve C of FIG. 4 of intermediate absorbance in the region 50 of the spectrum corresponds to an intermediate strength (in-laboratory value of 98.46 and IR-predicted value of 100.35 for a difference of 4.93%) whole printing ink. Finally, the curve B of FIG. 3 of higher absorbance in the region 50 of the spectrum corresponds to a lower strength (in-laboratory value of 87.45 and IR-predicted value of 91.76 for a difference of 1.92%) whole printing ink. The spectra are processed through a baseline correction between 2979 and 2712 $cm^{-1}$ and through a thickness correction between 2979 and 2712 $cm^{-1}$. The correlation between the spectra and the strength of the ink has been constructed in the region 50 between 1782 and 1485 $cm^{-1}$.

At a further level of analysis, data sets obtained through experimentation are stored into a database along with indications about features of their respective corresponding ink samples. Analysis performed by the software can determine a best fit between the set of spectral data corresponding to a currently evaluated sample and any set of spectral data stored in the database. Accordingly, successful matching with a set of spectral data of the database within previously defined tolerance criteria can lead to predicting features of the evaluated ink batch, including its behaviour and performance if introduced into a printing process. Appropriate decisions can then be made to accept or reject the evaluated printing ink supply and the corresponding supply of whole printing ink.

Turning now to FIG. 10, a further example of the method for evaluating whole printing ink samples will now be described. This method for evaluating whole printing ink samples can be used by a printing house (printer) to decide whether a received ink supply from an unknown batch should be introduced into a printing process.

Steps 1001 and 1002

A color printing ink sample is received from a whole printing ink supply.

Step 1003

A Fourier transform infrared (or eventually near-infrared) spectral analysis of the received sample is conducted.

Steps 1004 and 1005

An ink supply is accepted if the outcome of step 1003 for the corresponding sample is within previously defined tolerance criteria, else carrying out a standard testing procedure on more samples from the supply being out of tolerances (steps 1006-1010);

Steps 1006-1010

When an ink supply is not accepted at the outcome of step 1003, plant is advised to send the rest of the samples (step 1006) for further offset or gravure testing according to approved standard testing procedures (step 1007). If the results of the standard testing procedures are situated within tolerances (step 1008), the corresponding printing ink supply is accepted (step 1005). If the results of the standard testing procedures are situated out of tolerances, the ink supplied is again rejected or submitted to further testing.

Those of ordinary skill in the art will appreciate that the above-described illustrative embodiment of the present invention provides effective and practical solutions for the evaluation of a broad range of whole printing inks, including jet-printing ink, with unmatched functional and economic performance with respect to currently used solutions.

Therefore, it can be seen that the printing medium evaluation method according to the present invention can be advantageously used for ongoing control of the quality of ink supplies and their performance in printing processes, thus providing printing houses (printers) with better control over their ink supply expenses and enabling substantial cost reduction.

Other features of the non-restrictive illustrative embodiment of the printing medium evaluation method and device according to the present invention are the following:

A custom software can be implemented in the computer 15 or other computer connected to computer 15, to perform advanced comparison and analysis using stored sets of FT-IR and/or FT-NIR spectral data.

Elements such as 11, 13, 14, 18 and 44 of the testing apparatus (interferometer system 17 of FIG. 1) can be mounted in a sort of probe, wand or gun, remotely from computer 15 so as to enable direct access to a whole printing ink supply or sample nearby a printing press in a printing plant. Thereby, ink supplies can be conveniently evaluated on site by merely dipping an extremity of the probe into an ink supply to access a sample thereof and provide nearly immediate results.

The printing process may comprise at least one of the following processes: offset lithographic printing, flexographic printing, gravure or intaglio printing, (silk) screen printing, ink jet printing.

The non-restrictive illustrative embodiment of the present invention presents, amongst others, the following advantages:

The non-restrictive illustrative embodiment of the present invention provides a printing medium evaluation method that can be applied to a wide range of whole printing inks in the manufacturer supplied state, or in a diluted or bleached state.

The non-restrictive illustrative embodiment of the present invention provides a printing medium evaluation method that can be performed rapidly and economically with a very small volume of medium in an industrial plant.

The non-restrictive illustrative embodiment of the present invention provides a printing medium evaluation method that can be carried out offline, without requiring introduction of the evaluated medium into a printing process and generally without requiring mechanical or physical testing.

The non-restrictive illustrative embodiment of the present invention provides a printing medium evaluation method enabling acceptance or rejection of a printing ink supply according to the degree of compliance with a reference master ink (identification).

The non-restrictive illustrative embodiment of the present invention further provides a printing medium evaluation method that can provide indication of the performance of a printing ink in a printing process.

The non-restrictive illustrative embodiment of the present invention provides a printing medium evaluation method that can provide advanced indication of quality or performance problems associated with a printing ink.

The non-restrictive illustrative embodiment of the present invention provides a printing medium evaluation method that can provide quantitative characterization of functional, mechanical, chemical and/or physical parameters associated with a printing ink, by comparison with a training set or by direct parametric analysis.

The non-restrictive illustrative embodiment of the present invention still further provides a printing medium evaluation method that can generate substantial cost savings by ensuring ongoing compliance of ink supplies with reference quality standards.

Although the present invention has been described by way of a non-restrictive illustrative embodiment thereof, this embodiment can be modified at will, within the scope of the appended claims without departing from the spirit and scope of the present invention.

What is claimed is:

1. A method of evaluating a whole printing medium for use in a printing process, comprising:
   providing a set of predetermined spectral data indicative of performance-related features of reference whole printing media;
   submitting a sample of the whole printing medium to interferometric analysis thereby generating spectral data;
   analysing the generated spectral data, wherein analysis of the generated spectral data comprises evaluating features of the whole printing medium indicative of the performance of the whole printing medium in use in the printing process;
   comparing the evaluated features of the whole printing medium to the predetermined performance-related features of the reference whole printing media, thereby determining the performance of the whole printing medium in the printing process; and
   performing one of (i) selecting and (ii) rejecting the whole printing medium for use in the printing process according to the determined performance thereof.

2. A method of evaluating a whole printing medium as defined in claim 1, wherein interferometric analysis comprises FT-IR interferometric analysis.

3. A method of evaluating a whole printing medium as defined in claim 1, wherein interferometric analysis comprises FT-NIR interferometric analysis.

4. A method of evaluating a whole printing medium as defined in claim 1, wherein interferometric analysis comprises irradiating the sample of whole printing medium with light in a specific spectral range of the infrared spectrum.

5. A method of evaluating a whole printing medium as defined in claim 1, wherein interferometric analysis comprises irradiating the sample of whole printing medium with light in a specific spectral range of the near-infrared spectrum.

6. A method of evaluating a whole printing medium as defined in claim 1, wherein interferometric analysis comprises:
   submitting the sample of whole printing medium to FT-IR interferometric analysis;
   submitting the sample of whole printing medium to FT-NIR interferometric analysis; and obtaining different and complementary spectral data from (a) the FT-IR interferometric analysis and (b) the FT-NIR interferometric analysis.

7. A method of evaluating a whole printing medium as defined in claim 1, wherein interferometric analysis comprises:
   irradiating the sample of whole printing medium with light having a predetermined frequency characteristic;
   detecting a radiation response from the irradiated sample of whole printing medium; and
   extracting the spectral data from the radiation response.

8. A method of evaluating a whole printing medium as defined in claim 7, wherein irradiating the sample of whole printing medium with light comprises directing light radiation toward the sample of whole printing medium at an angle and detecting a radiation response comprises collecting a reflected scattered light radiation response.

9. A method of evaluating a whole printing medium as defined in claim 7, wherein irradiating the sample of whole printing medium comprises propagating light through the whole printing medium and detecting a radiation response comprises collecting a scattered radiation response produced by the light propagated through the sample of whole printing medium.

10. A method of evaluating a whole printing medium as defined in claim 7, wherein generating spectral data further comprises enclosing the sample of whole printing medium in a gas-tight enclosure to prevent evaporation of volatile components and thereby obtain maximal information.

11. A method of evaluating a whole printing medium as defined in claim 1, wherein generating spectral data comprises:
    generating light having a predetermined frequency characteristic;
    irradiating the sample of whole printing medium with the generated light having a predetermined frequency characteristic;
    selectively absorbing energy from the irradiating light through the whole printing medium;
    producing from energy of the irradiating light not absorbed by the whole printing medium a time distributed radiation response related to properties of the whole printing medium;
    collecting the time distributed radiation response;
    converting the collected time distributed radiation response to an analog response signal;
    converting the analog response signal to a digital response signal;
    supplying the digital response signal to a computer to provide a time domain response; and
    in the computer, mathematically converting the time domain response to a frequency domain response by a time-to-frequency domain transformation to thereby produce the spectral data.

12. A method of evaluating a whole printing medium as defined in claim 11, further comprising representing the spectral data under the form of an energy/frequency pattern.

13. A method of evaluating a whole printing medium as defined in claim 11, further comprising representing the spectral data under the form of a graph of absorbance versus wave number.

14. A method of evaluating a whole printing medium as defined in claim 11, wherein said whole printing medium is whole printing ink, jet printing ink or a dye.

15. A method of evaluating a whole printing medium as defined in claim 1, wherein generating spectral data comprises producing a set of FT-IR data and detecting spectral data indicative of features of the whole printing medium related to performance of the whole printing medium in the printing process comprises comparing the produced FT-IR data with a reference set of FT-IR data obtained from reference whole printing media.

16. A method of evaluating a whole printing medium as defined in claim 15, wherein analysis of the spectral data further comprises accepting or refusing the whole printing medium for use in the printing process in response to the whole printing medium performance prediction, and accepting or refusing the whole printing medium comprises:
    defining tolerance criteria by reference to deviations between the produced FT-IR data and the reference set of FT-IR data;
    applying the tolerance criteria to the deviations between the produced FT-IR data and the reference set of FT-IR data; and accepting the whole printing medium for use in the printing process when the deviations between the produced FT-IR data and the reference set of FT-IR data are situated within limits established by the tolerance criteria.

17. A method of evaluating a whole printing medium as defined in claim 16, wherein defining tolerance criteria comprises:
obtaining a reference set of spectral data for a plurality of whole printing media of slightly different chemical compositions;
obtaining information relating to the physical, mechanical and functional properties of the plurality of whole printing media of slightly different chemical composition;
correlating the reference set of spectral data with the physical, mechanical and functional properties of the plurality of whole printing media of slightly different chemical composition to produce a correlated set of spectral data; and
determining the impact on the physical, mechanical and functional properties of the whole printing medium of deviations from the correlated set of spectral data.

18. A method of evaluating a whole printing medium as defined in claim 17, wherein said whole printing medium is whole printing ink, jet printing ink or a dye.

19. A method of evaluating a whole printing medium as defined in claim 1, wherein determining whole printing medium performance also comprises constructing training sets of spectral data for each of a plurality of whole printing medium parameters and indicating variations of the spectral data corresponding to variations of said whole printing medium parameters.

20. A method of evaluating a whole printing medium as defined in claim 1, wherein determining whole printing medium performance comprises:
identifying areas of currently generated and reference sets of spectral data in which deviations occur; and
associating the deviations with features of the whole printing medium indicative of potential problems or compromised performance if introduced into the printing process.

21. A method of evaluating a whole printing medium as defined in claim 1, wherein determining whole printing medium performance further comprises:
obtaining, through experimentation, sets of spectral data corresponding to printing media having known properties;
storing the sets of spectral data obtained through experimentation along with indications about the features of the respective printing media; and
evaluating spectral data from the whole printing medium in response to the sets of spectral data.

22. A method of evaluating a whole printing medium as defined in claim 21, wherein said whole printing medium is whole printing ink, jet printing ink or a dye.

23. A method of evaluating a whole printing medium as defined in claim 1, wherein said whole printing medium is whole printing ink, jet printing ink or a dye.

24. A method of evaluating a whole printing medium as defined in claim 1, wherein the whole printing medium performance prediction comprises:
identifying areas of currently generated and reference sets of spectral data in which deviations occur; and
associating the deviations with features of the whole printing medium indicative of potential problems and compromised performance if introduced into the printing process.

25. A device for evaluating a whole printing medium for use in a printing process, comprising means for generating spectral data from a sample of the whole printing medium and means for analysing the spectral data, wherein the analysing means comprises:
means for detecting spectral data indicative of features of the whole printing medium related to performance of the whole printing medium in the printing process; and
means for predicting the performance of the whole printing medium in the printing process in response to a set of spectral data indicative of performance-related features of reference whole printing media.

26. A device for evaluating a whole printing medium as defined in claim 25, wherein the analysing means further comprises means for accepting or refusing the whole printing medium for use in the printing process in response to the whole printing medium performance prediction.

27. A device for evaluating a whole printing medium as defined in claim 25, wherein said whole printing medium is whole printing ink, jet printing ink or a dye.

28. A device for evaluating a whole printing medium for use in a printing process, comprising a generator of spectral data from a sample of the whole printing medium, the generator comprises an interferometric analysis system, and an analyser of the spectral data, wherein the analyser comprises:
a detector of the spectral data indicative of features of the whole printing medium related to performance of the whole printing medium in the printing process; and
a predictor of the performance of the whole printing medium in the printing process in response to a set of spectral data indicative of performance-related features of reference whole printing media.

29. A device for evaluating a whole printing medium as defined in claim 28, wherein the analyser comprises a decision-making computer system for accepting or refusing the whole printing medium for use in the printing process in response to the prediction of the performance of the whole printing medium conducted by the predictor.

30. A device for evaluating a whole printing medium as defined in claim 28, wherein the interferometric analysis system comprises a FT-IR interferometric analysis system.

31. A device for evaluating a whole printing medium as defined in claim 28, wherein the interferometric analysis system comprises a FT-NIR interferometric analysis system.

32. A device for evaluating a whole printing medium as defined in claim 28, wherein the interferometric analysis system comprises a source of light in a specific spectral range of the infrared spectrum for irradiating the sample of whole printing medium.

33. A device for evaluating a whole printing medium as defined in claim 28, wherein the interferometric analysis system comprises a source of light in a specific spectral range of the near-infrared spectrum for irradiating the sample of whole printing medium.

34. A device for evaluating a whole printing medium as defined in claim 28, wherein the interferometric analysis system comprises:
a FT-IR interferometric analysis system;
a FT-NIR interferometric analysis system; and
a compiler of different and complementary spectral data from (a) the FT-IR interferometric analysis system and (b) the FT-NIR interferometric analysis system.

35. A device for evaluating a whole printing medium as defined in claim 28, wherein the generator further comprises:
- a source of light having a predetermined frequency characteristic for irradiating the sample of whole printing medium;
- a detector of radiation response from the irradiated sample of whole printing medium; and
- an extractor of the spectral data from the radiation response.

36. A device for evaluating a whole printing medium as defined in claim 35, further comprising a portable probe unit incorporating the source of light and the detector of radiation response for remotely probing a whole printing medium on site.

37. A device for evaluating a whole printing medium as defined in claim 35, wherein the source of light is oriented for directing light radiation toward the sample of whole printing medium at an angle and a the detector of a radiation response comprises a collector of reflected scattered light radiation response.

38. A device for evaluating a whole printing medium as defined in claim 35, wherein the source of light is oriented for propagating light through the sample of whole printing medium and the detector of radiation response comprises a collector of scattered radiation produced by light propagated through the sample of whole printing medium.

39. A device for evaluating a whole printing medium as defined in claim 28, wherein the generator of spectral data further comprises a gas-tight enclosure for enclosing the sample of whole printing medium to prevent evaporation of volatile components and thereby obtain maximal information.

40. A device for evaluating a whole printing medium as defined in claim 28, wherein the generator of spectral data is a generator of FT-IR data and the detector of the spectral data indicative of features of the whole printing medium related to performance of the whole printing medium in the printing process comprises a feature allowing comparison of the produced FT-IR data with a reference set of FT-IR data obtained from a reference whole printing media.

41. A device for evaluating a whole printing medium as defined in claim 40, wherein the analyser further comprises:
- means for defining tolerance criteria by reference to deviations between the generated FT-IR data and the reference set of FT-IR data;
- means for applying the tolerance criteria to the deviations between the generated FT-IR data and the reference set of FT-IR data; and
- means for accepting the whole printing medium for use in the printing process when the deviations between the generated FT-IR data and the reference set of FT-IR data are within the limits established by the tolerance criteria.

42. A device for evaluating a whole printing medium as defined in claim 41, wherein the means for defining tolerance criteria comprises:
- means for obtaining a reference set of spectral data for a plurality of printing media of slightly different chemical compositions;
- means for obtaining information relating to the physical, mechanical or functional properties of the plurality of printing media of slightly different chemical compositions;
- means for correlating the reference set of spectral data with the physical, mechanical or functional properties of the plurality of printing media of slightly different chemical compositions to produce a correlated set of spectral data; and
- means for determining the impact on the physical, mechanical or functional properties of the whole printing medium of deviations from the correlated set of spectral data.

43. A device for evaluating a whole printing medium as defined in claim 41, wherein the means for defining tolerance criteria comprises:
- means for obtaining a reference set of spectral data for a plurality of printing media of slightly different chemical compositions;
- means for obtaining information relating to the physical, mechanical and functional properties of the plurality of printing media of slightly different chemical compositions;
- means for correlating the reference set of spectral data with the physical, mechanical and functional properties of the plurality of printing media of slightly different chemical compositions to produce a correlated set of spectral data; and
- means for determining the impact on the physical, mechanical and functional properties of the whole printing medium of deviations from the correlated set of spectral data.

44. A device for evaluating a whole printing medium as defined in claim 42, wherein said whole printing medium is whole printing ink, jet printing ink or a dye.

45. A device for evaluating a whole printing medium as defined in claim 28, wherein the predictor comprises:
- means for constructing training sets of spectral data for each of a plurality of whole printing medium parameters; and
- means for indicating variations of the spectral data corresponding to variations of the whole printing medium parameters.

46. A device for evaluating a whole printing medium as defined in claim 28, wherein the predictor comprises:
- means for identifying portions of a currently generated and reference sets of spectral data in which deviations occur; and
- means for associating the deviations with features of the whole printing medium indicative of performance in the printing process.

47. A device for evaluating a whole printing medium as defined in claim 28, wherein the predictor comprises:
- means for obtaining, through experimentation, sets of spectral data corresponding to printing media having known properties;
- means for storing the sets of spectral data obtained through experimentation along with indications about the features of the respective printing media; and
- means for evaluating spectral data from the whole printing medium in response to the sets of spectral data.

48. A device for evaluating a whole printing medium as defined in claim 47, wherein said whole printing medium is whole printing ink, jet printing ink or a dye.

* * * * *